United States Patent [19]

Wright

[11] Patent Number: 5,516,513
[45] Date of Patent: May 14, 1996

[54] BIOLOGICAL OVICIDE FOR CONTROL OF LEPIDOPTEROUS INSECTS

[75] Inventor: James C. Wright, Cave Creek, Ariz.

[73] Assignee: Troy Biosciences, Inc., Phoenix, Ariz.

[21] Appl. No.: 274,701

[22] Filed: Jul. 14, 1994

[51] Int. Cl.$^6$ ..................... A01N 63/04
[52] U.S. Cl. .............. 424/93.3; 424/93.5; 424/405; 435/254.1; 435/911
[58] Field of Search ............... 424/93.3, 93.5, 424/405; 435/254.1, 911

[56] References Cited

U.S. PATENT DOCUMENTS 5,413,784  5/1995  Wright et al. ................ 435/93.5

OTHER PUBLICATIONS

Cheung et al "Jour Invertebr Pathol" 1982 (39) 3 303–313.

Primary Examiner—Herbert J. Lilling
Attorney, Agent, or Firm—Banner & Allegretti, Ltd.

[57] ABSTRACT

An agricultural formulation of a virulent isolate of Beauveria bassiana, which has the characteristics of B. bassiana ATCC 74040, can be used to effectively control lepidopterous insects. This fungal strain has been found to be active against the egg stage of lepidopterans. Activity against the larval stages of lepidopterans is also shown.

11 Claims, No Drawings

BIOLOGICAL OVICIDE FOR CONTROL OF LEPIDOPTEROUS INSECTS

FIELD OF THE INVENTION

The invention is directed to a method of controlling pests, in particular insect pests belonging to the Order Lepidoptera, using a biopesticidal composition containing a highly virulent entomopathogenic fungus of the species *Beauveria bassiana*.

BACKGROUND OF THE INVENTION

Larvae of lepidopterous insects cause millions of dollars of damage each year to agricultural crops grown for food and fiber production. While chemical insecticides such as chlorinated hydrocarbons, organophosphorus compounds, carbamates, and synthetic pyrethroids are conventionally used to control these insects, most species are broadly and highly resistant to chemical insecticides due to the continued reliance upon such substances by producers in order to prevent crop damage and consequent economic losses.

Application of these largely ineffective chemicals have significant impact upon the environment in which they are placed. In addition to environmental pollution, use of chemical insecticides create potential health hazards for agricultural workers and consumers. The problem of residues on consumer products and water quality present major drawbacks. Detrimental effects of these chemical insecticides on nontarget species often result in secondary pest outbreaks. Moreover, such chemicals are often phytotoxic to exposed plants.

Because of the problems associated with the use of chemical pesticides, safer and more effective methods of controlling insect pests are essential for continued agricultural production. While biological control agents are a reasonable alternative to chemical pesticides, none have been identified as being commercially feasible for controlling lepidopterous pests by direct activity against the egg stage. *Bacillus thuringenis*, for example, is an biological control agent designed specifically as an insecticide for control of certain leaf-eating caterpillars (Lepidoptera). The active ingredient is a stomach poison and, as such, must be eaten by the larvae to be effective. Larvae of lepidopterous insects must, therefore, be actively feeding on treated exposed plant parts.

Recently the development of mycoinsecticides have been directed towards specific insects such as *Bemisia tabaci*. No mycoinsecticide has, however, been heretofore identified as having ovicidal activity.

SUMMARY OF THE INVENTION

The invention is directed to the use of a highly virulent strain of an entomopathogenic fungus to control lepidopterous insects which attack and damage plants. It has been discovered that a strain of *Beauveria bassiana* having the characteristics of *Beauveria bassiana* ATCC 74040, shows virulence against the egg stage as well as the larval stages of lepidopterous insects. The entomopathogenic fungus used in the practice of the invention is a *B. bassiana* culture having the characteristics of *B. bassiana* ATCC 74040, and mutants thereof which substantially retain the virulence of the parent strain. The use of this fungus as a mycoinsecticide does not produce the hazards associated with conventional chemical control agents. The fungus can be applied directly to the eggs or larvae of insects or to the plants which are to be protected.

It is an object of the invention to provide a method of controlling lepidopterous insect pests. The method comprises applying a pesticidal composition containing a fungus having the identifying characteristics of *B. bassiana* ATCC 74040 to lepidopterous insects or to the foliage of plants to be protected.

*B. bassiana* having the identifying characteristics of *B. bassiana* ATCC 74040 has been found to be virulent against the egg stages of lepidopterous species of insects as well as to the larvae thereof. The method of the invention has been found to be particularly advantageous when the pesticidal composition is applied to lepidopterous insects in the egg stage.

DETAILED DESCRIPTION OF THE INVENTION

Chemical insecticides and some biological insecticides are currently employed in the control of insect pests. These have associated problems and are not completely effective. Because of the problems associated with the use of chemical pesticides, safer and more effective methods of controlling insect pests are needed. There is a need for alternative materials that can be used in a complementary fashion with existing controls and which can replace existing control agents that may lose efficacy due to resistance or other factors.

The development of a broad spectrum of pesticides would reduce the need for many of the petrochemically based pesticides. While biological control agents have been tried, their availability, limited host range, cost and reliability have reduced the potential for implementing the use of these biological control agents. By using fungi to control insect pests, the potential for resistance development is minimized, which, in turn, will stabilize many pest management programs.

At least six species of Beauveria are recognized based on morphological and biochemical characteristics: *B. alba, B. amorpha, B. bassiana, B. brongniartii, B. velata,* and *B. Vermiconia* (Mugnai et al., 1989, A chemotaxonomic evaluation of the genus Beauveria. *Mycol. Res.*, 92:199–209). Not only do significant differences exist between species of Beauveria, but significant intraspecies variability exist as well. Different strains of *B. bassiana* are known to exhibit different insecticidal effects. As disclosed by Peczyńska-Czoch et al. (Formation of beauvericin by selected strains of *Beauveria bassiana*, 1991, *Archivum Immunologiae et Therapiae Experimentalis*, 39:175–179), significant intraspecies variability of *B. bassiana* isolates exist. Ferron (Pest control by the Fungi Beauveria and Metarhizium, In: Microbial Control of Pest and Plant Diseases, 1970–1980, Burges, Ed., 1981, Academic Press, pp. 465–4820) not only discloses that it is known that entomopathogenic fungi have certain specificity, but also discloses that within the same species of fungus different strains can have different activity spectra. Reference is also made to Ferron, Biological Control of Insect Pests by Entomogenous Fungi, 1978, *Ann. Rev. Entomol.*, 23:409–442, which also discloses that different fungal strains have different activity spectrum.

It has been discovered that a strain of *Beauveria bassiana* having the characteristics of *Beauveria bassiana* ATCC 74040, shows virulence against the egg stage as well as the larval stages of lepidopterous insects. The entomopathogenic fungus used in the practice of the invention is a *B. bassiana* culture having the characteristics of *B. bassiana* ATCC 74040, and mutants thereof which substantially retain the virulence of the parent strain. A biologically pure culture of an isolate of *Beauveria bassiana* was deposited under Accession No. ATCC 74040 in the American Type Culture Collection (ATCC), 12301 Parklawn Drive, Rockville, Md. 20852, on Mar. 11, 1991. This isolate has also been deposited in the USDA—ARS Collection of Entomopathogenic Fungal Culture under Accession No. ARSEF 3097. This strain, which was isolated from a boll weevil cadaver in the lower Rio Grande Valley of Texas, has been confirmed to be a *B. bassiana* (Balsamo) Vuillemin.

The taxonomic description of *Beauveria bassiana* ATCC 74040 is the same as that for other members of the species *B. bassiana*. *B. bassiana* is an imperfect fungus (Fungi Imperfect) of the subdivision Deuteromycotonia. The genus Beauveria Vuill is within the Class Deuteromycetes and is distinguished from other genera by having conidia that are borne singly, not catenulate. The fertile portion of the conidiophore is zigzag in shape and drawn out at the tip. The species *B. bassiana* has spherical, not ellipsoid, conidia measuring 2 to 3 micrometers by 2 to 2.5 micrometers and with conidiophores forming dense bunches.

Like most entomogenous fungi, *B. bassiana* initiates infection by a germinating spore (conidium) attaching to and subsequently penetrating the cuticle of the insect host. *B. bassiana* ATCC 74040 attaches very securely to the cuticle of the targeted insect pest and is typically not removed by the grooming activities thereof. While not wishing to be bound by any particular theory, this may account somewhat for the high virulence of the fungus. As the fungus penetrates the target pest cuticle, the invasive hyphae begin to enter the host tissues and ramify through the hemocoel. Hyphal bodies or segments of the hyphae distribute throughout the hemocoel, filling the dying insect with mycelium. Emergent hyphae grow out through the insects integument and produce spores on the external surface of the host. These spores, or conidia, are dispersed and capable of infecting new host insect pests. Although the mode of infection of *Beauveria bassiana* fungi is generally by cuticular penetration by the germ tube of the fungal conidia and may also occur through the respiratory or alimentary tract (such as mouth parts). Ingestive fungal spores voided in the feces may provide another source of contact with the cuticle of the targeted insect pest. Death of the host may occur either by release of fungal toxins or by tissue destruction.

While *B. bassiana* ATCC 74040 is taxonomically the same as other members of the species *B. bassiana*, this isolate differs from other members of its species metabolically and biochemically. *B. bassiana* having the characteristics of *B. bassiana* ATCC 74040 has been heretofore found to be highly virulent against *Anthonomus grandis* (boll weevils), *Bemisia tabaci* (sweet potato whiteflies) and *Pseudatomoscellis seriatus* (cotton fleahoppers). Reference is made to copending application Ser. No. 08/058,795, the disclosure of which is incorporated herein by reference. *B. bassiana* ATCC 74040 has also been observed by the inventor to have mycobiological activity against citrus mealybug, *Planococcus citri;* thrips, Frankliniella spp.; onion thrips, *Thrips tabaci;* armyworms, Spodoptera spp.; Colorado potato beetle, *Leptinotarsa decemlineata;* two spotted spider mite, *Tetranychus urticae;* gypsy moth, *Lymantria dispar;* pepper weevil, *Anthonomus eugenii;* webworms, Pyralididae; corn rootworms, Diabrotica app.; flies, Muscidae; chinch bugs, Blissus spp.; corn borers, Diatraea spp.; and other pests.

It has now been discovered that this isolate is highly virulent to the eggs of a number of important lepidopterous pests. Such insect pests include *Heliothis virescens, Heliocoverpa zea, Spodoptera frugiperda, Trichoplusie ni* and *Plutella xylostella*. The use of this fungus as a mycoinsecticide does not produce the hazards associated with conventional chemical control agents. The fungus can be applied directly to the eggs or larvae of insects or to the plants which are to be protected.

Prior to applicant's discovery of *Beauveria bassiana* ATCC 74040, a *Beauveria bassiana* species having effectiveness required for commercial use was not known. Although the potential for commercial exploitation of entomopathogenic fungi as an insecticide has been explored, various factors such as the virulence of the strain, the susceptibility of the host insect and the mode of infectivity (i.e., not only through the gut but through spiracles and, in particular, through integument) have deterred the formulation of a commercially effective product. For example, all possible ways of infection are not necessarily exploited by a given fungus for a given insect. In addition, conditions encountered in the field, such as humidity and temperature, must be considered.

The inventor was the first to produce a commercially useful biopesticide containing *B. bassiana*, specifically *B. bassiana* ATCC 74040, as required for use in the claimed invention. Reference is made to the product (NATURALIS®) described by Knauf and Wright ("Fermone Exp 7744: A Biorational Insecticide for Whitefly Control. A Review of Research and Cooperator Trials in Florida and Texas Greenhouses," 1992, and "A Summary of Research and Cooperator Studies of Naturalis®-L and Fermone Exp 7744 Bioinsecticides for Control of Sweet Potato Whitefly," 1992).

The fungus used to practice the method of the invention can be successfully grown on several different media including potato dextrose agar (PDA), Subraund dextrose agar (SDA), oatmeal agar, and mixed bran agar. Based on the diameter of the colonies, spore production, and the cost and availability of the agars, SDA provides an excellent medium for growing the fungus. The *B. bassiana* used in the practice of the invention may be cultured and mass produced by methods used to culture Beauveria spp. See for example, U.S. Pat. No. 4,925,663; *Microbial Control of Pest and Plant Diseases* 1970–1980, published by Academic Press, pp. 471–473 (1981; edited by H. D. Burges); and Feng et al., *J. Invertebrate Pathology,* Vol. 46, no. 3, November 1985, page 260, the disclosures of which are incorporated herein by reference. The fungal growth range is between 40° and 95° F. in a wide range of humidity with high humidity necessary to germinate spores and to increase spore production. The concentration of *B. bassiana* used in the composition is readily determinable of skilled practitioners depending, for example, on the extent and degree of infestation, time, weather conditions, life cycle stage of the pest, and concurrent usage of other insecticides. Generally $2 \times 10^5$ to $2 \times 10^{14}$ spores per milliliter, preferably, at least about $2 \times 10^8$ spores per milliliter, is sufficient to control lepidopterous insect pests.

The composition used to practice the invention may consist of *B. bassiana* alone, or may comprise *B. bassiana* in combination with a conventional agriculturally acceptable carrier. Solid and liquid formulations may be used. Additional expedients used in the art, such as emulsifiers, thickeners, foaming agents, etc., may be used. The composition may also include other chemical or biological control agents. Particularly advantageous is the use of a formulation comprising *B. bassiana* having the identical characteristics of ATCC 74040 and *B. thuringenis*. Compositions may also be applied, either simultaneously or sequentially, with other chemical or biological control agents. Application of conventional chemical insecticides, at a reduced rate, combined with fungal compositions has been found by the inventor to impact damaging insect populations at a faster rate than when the fungus is applied alone. Application of the fungal composition may be accomplished using standard operating equipment used in the agricultural industry by conventional ground spreaders or sprayers, or aerially.

Field evaluations in Mississippi, Louisiana and Texas have confirmed the biological activity of *B. bassiana* ATCC 74040 against the egg stage of lepidopterous pests. When lepidopterous eggs are exposed to *B. bassiana* ATCC 74040 the eggs are killed when the fungus colonizes the egg. Timing of application is important in relationship to the age of the egg, as newly oviposited eggs are more susceptible to the virulent activity of *B. bassiana* ATCC 74040. The fungus, however, also will colonize larvae when exposed directly or when newly hatched larvae feed on the egg shell from which it emerged. This activity gives immediate and long term control of the pests.

The following Examples demonstrate the activity of *B. bassiana* ATCC 74040 against the eggs of important lepidopterous species and also related activity against larvae. The data reported in the following Tables is the average of three trials. One hundred insects (eggs or larva) being treated in each trial.

EXAMPLE 1

Eggs of *Heliothis virescens* were treated with different concentrations of *B. bassiana* spores. The percent mortality is shown in Table 1.

TABLE 1

| Concentration (no. of spores/ml) | % of eggs colonized |
| --- | --- |
| $2.5 \times 10^5$ | 58 |
| $2.5 \times 10^6$ | 56 |
| $2.5 \times 10^7$ | 70 |
| $1.0 \times 10^8$ | 90 |

EXAMPLE 2

Eggs of *Heliocoverpa zea* were treated with different concentrations of *B. bassiana* spores. The percent mortality is shown in Table 2.

TABLE 2

| Concentration (no. of spores/ml) | % of eggs colonized |
| --- | --- |
| $2.5 \times 10^5$ | 39 |
| $2.5 \times 10^6$ | 38 |
| $2.5 \times 10^7$ | 36 |
| $1.0 \times 10^8$ | 59 |

EXAMPLE 3

Eggs of *Spodoptera frugiperda* were treated with different concentrations of *B. bassiana* spores. The percent mortality is shown in Table 3.

TABLE 3

| Concentration (no. of spores/ml) | % of eggs colonized |
| --- | --- |
| $2.5 \times 10^5$ | 73 |
| $2.5 \times 10^6$ | 65 |
| $2.5 \times 10^7$ | 80 |
| $1.0 \times 10^8$ | 88 |

EXAMPLE 4

Eggs of *Trichoplusia ni* were treated with different concentrations of *B. bassiana* spores. The percent mortality is shown in Table 4.

TABLE 4

| Concentration (no. of spores/ml) | % of eggs colonized |
| --- | --- |
| $2.5 \times 10^5$ | 18 |
| $2.3 \times 10^6$ | 21 |
| $2.5 \times 10^7$ | 16 |
| $1.0 \times 10^8$ | 44 |

EXAMPLE 5

Eggs of *Plutella xystella* were treated with different concentrations of *B. bassiana* spores. The percent mortality is shown in Table 5.

TABLE 5

| Concentration (no. of spores/ml) | % of eggs colonized |
| --- | --- |
| $5.0 \times 10^7$ | 56 |
| $1.0 \times 10^8$ | 50 |

EXAMPLE 6

Larvae, first and second instar of *Heliothis virescens* were treated with different concentrations of *B. bassiana*. The percent mortality is shown in Table 6.

TABLE 6

| Concentration (no. of spores/ml) | % of larvae colonized |
| --- | --- |
| $2.5 \times 10^6$ | 13 |
| $2.5 \times 10^7$ | 13 |
| $1.0 \times 10^8$ | 19 |

EXAMPLE 7

Larvae, third and fourth instar of *Heliothis virescens* were treated with different concentrations of *B. bassiana*. The percent mortality is shown in Table 7.

TABLE 7

| Concentration (no. of spores/ml) | % of larvae colonized |
| --- | --- |
| $8.4 \times 10^8$ | 75 |
| $1.2 \times 10^9$ | 76 |
| $1.5 \times 10^9$ | 76 |
| $1.9 \times 10^9$ | 78 |

EXAMPLE 8

Larvae, first and second instar of *Heliocoverpa zea* were treated with different concentrations of *B. bassiana*. The percent mortality is shown in Table 8.

TABLE 8

| Concentration (no. of spores/ml) | % of eggs colonized |
|---|---|
| $2.4 \times 10^7$ | 42 |
| $1.2 \times 10^8$ | 64 |
| $2.4 \times 10^9$ | 48 |

It will be understood that the foregoing examples are for purposes of illustration only and are not meant to limit the scope of the claimed invention. Various changes in the details, materials and arrangement of parts which have been described and illustrated herein in order to explain the nature of the invention may be made by those skilled in the art within the principle and scope of the invention as expressed in the appended claims.

I claim:

1. A method of controlling lepidopterous insect pests comprising applying to said insect pests or to plant foliage a composition containing *B. bassiana* ATCC 74040 or mutants thereof which shows virulence against the egg stage and larval stages of lepidopterous insects.

2. The method of claim 1 wherein said composition further contains an agriculturally acceptable carrier.

3. The method of claim 2 wherein said fungus is in the form of spores.

4. The method of claim 2 wherein said composition contains $2 \times 10^8$ to $2 \times 10^{14}$ spores *B. bassiana* per milliliter of carrier.

5. The method of claim 1 wherein said insect pest is in the form of eggs.

6. The method of claim 1 wherein said insect pest is in the form of larvae.

7. The method of claim 1 wherein said lepidopterous insect pest is selected from the group consisting of *Heliothis virescens, Heliocoverpa zea, Spodoptera frugiperda, Trichoplusie ni* and *Plutella xylostella*.

8. The method of claim 1 wherein said composition further contains at least one additional insecticide.

9. The method of claim 8 wherein said at least one additional insecticide is a chemical insecticide.

10. The method of claim 8 wherein said at least one additional insecticide is a biological insecticide.

11. The method of claim 10 wherein said biological insecticide comprises *Bacillus thuringenis*.

* * * * *